United States Patent
Nokihara et al.

(10) Patent No.: US 8,455,400 B2
(45) Date of Patent: Jun. 4, 2013

(54) SUBSTRATE FOR BIOCHIP AND BIOCHIP

(75) Inventors: Kiyoshi Nokihara, Kyoto (JP); Yasuo Oka, Fuji (JP)

(73) Assignees: Hipep Laboratories, Kyoto (JP); Nippon Light Metal Company, Ltd., Tokyo (JP)

(*) Notice: Subject to any disclaimer, the term of this patent is extended or adjusted under 35 U.S.C. 154(b) by 1253 days.

(21) Appl. No.: 11/915,366

(22) PCT Filed: May 24, 2006

(86) PCT No.: PCT/JP2006/310313
§ 371 (c)(1),
(2), (4) Date: Nov. 23, 2007

(87) PCT Pub. No.: WO2006/126568
PCT Pub. Date: Nov. 30, 2006

(65) Prior Publication Data
US 2010/0184622 A1    Jul. 22, 2010

(30) Foreign Application Priority Data

May 24, 2005    (JP) .................. 2005-150330

(51) Int. Cl.
C40B 40/04    (2006.01)
C40B 50/14    (2006.01)
B32B 15/00    (2006.01)

(52) U.S. Cl.
USPC .............................. 506/15; 506/30; 428/457

(58) Field of Classification Search
None
See application file for complete search history.

(56) References Cited

U.S. PATENT DOCUMENTS
7,155,934 B2    1/2007    Lauten-Schlaeger

FOREIGN PATENT DOCUMENTS

| JP | 2001-128683 | A |   | 5/2001 |
| JP | 2002-526755 | A |   | 8/2002 |
| JP | 2004-045201 |   | * | 2/2004 |
| JP | 2004-45201  | A |   | 2/2004 |
| JP | 2004-149814 | A |   | 5/2004 |
| JP | 2005-43312  | A |   | 2/2005 |
| JP | 2005-510440 | A |   | 4/2005 |

(Continued)

OTHER PUBLICATIONS

Azumi (May 12, 2003) Journal of The Electrochemical Society vol. 150 pp. C461 to C464.*

(Continued)

*Primary Examiner* — Ardin Marschel
*Assistant Examiner* — Christian Boesen
(74) *Attorney, Agent, or Firm* — Birch, Stewart, Kolasch & Birch, LLP

(57) ABSTRACT

A substrate for biochips with which immobilization is easy, which does not exhibit self-fluorescence, which is easy to manufacture, and which is excellent in flatness and surface precision, is disclosed. A substrate having a substrate body of the biochip, which is made of a metal, and a carbon layer having functional groups formed on the metal substrate body is used as a substrate for biochips. Since the substrate body of the substrate for biochips is made of a metal, the substrate is not only easy to manufacture, but also free from cracking and chipping, so that it allows easy handling, and high flatness and surface precision can be attained. Therefore, the problem that the optical system is hard to focus when detecting fluorescence does not occur. Moreover, since the substrate body is made of a metal, it does not emit fluorescence by itself. In addition, since the carbon layer has functional groups such as amino groups, biologically relevant substances can be easily immobilized.

5 Claims, 1 Drawing Sheet

FOREIGN PATENT DOCUMENTS

| WO | WO 00/16893 A2 | 3/2002 |
|---|---|---|
| WO | WO-02/31502 A | 4/2002 |
| WO | WO 02/31502 A1 * | 4/2002 |
| WO | WO-03/045862 A2 | 6/2003 |
| WO | WO 03/045862 A2 | 6/2003 |
| WO | WO 2005/010525 A1 * | 2/2005 |
| WO | WO 2005-010525 A2 | 2/2005 |

OTHER PUBLICATIONS

Tanga (Apr. 18, 2002) PCT International Patent Application Publication WO 02/031502 A1 machine translation.*

Donpou (Feb. 12, 2004) Japanese Patent JP 2004-045201 machine translation.*

Tanga (Feb. 17, 2005) PCT International Patent Application Publication WO 2005/010525 A1 machine translation.*

Frey et al. (Jun. 20, 2003) IEEE ISCAS Proceedings of the 2003 International Symposium on Circuits and Systems vol. 5 pp. V9 to V12.*

Tanga et al. (Apr. 18, 2002) PCT International Patent Application Publication WO 02/031502 A1 certified translation.*

The Free Dictionary (downloaded Jul. 11, 2012 from http://www.thefreedictionary.com/Polish) main entry for polish p. 1.*

Kim, Do Hyung; "Anisotropic Tribological Properties of the Coating on a Magnetic Recording Disk;" Thin Solid Films 360; (2000); pp. 187-194.

Lu, Chung-Jen; "Nano-Tribological Investigations of Carbon Overcoats; Correlation with Raman Spectra;" Thin Solid Films 268; (1995); pp. 83-90.

Stafford, K. N.; "Electroless Nickel Coatings: Their Application, Evaluation & Production Techniques;" Materials & Design vol 3.; Dec. 1982; pp. 608-614.

Supplementary European Seach Report for corresponding European application (EP06756519), Mar. 8, 2012.

* cited by examiner

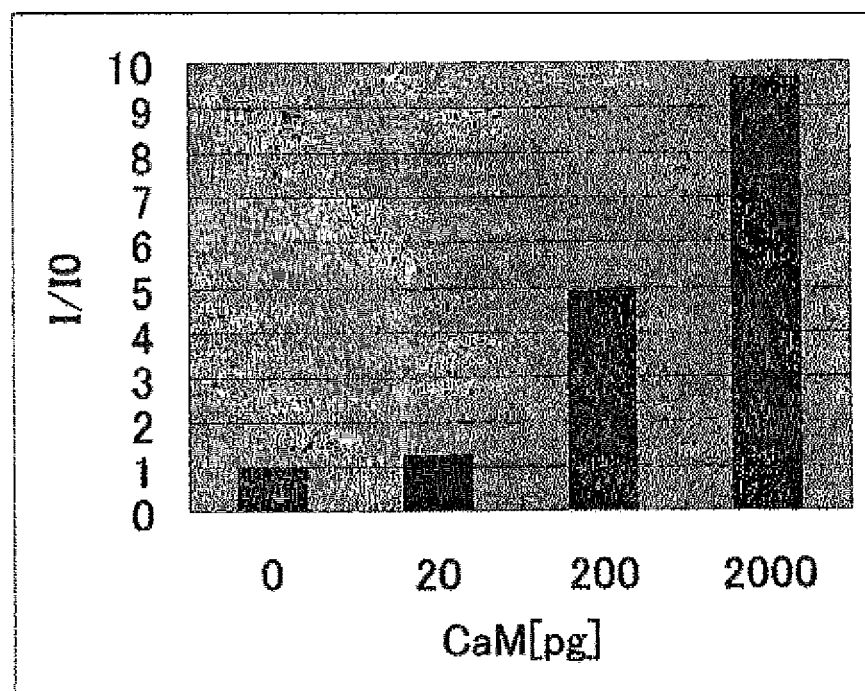

SUBSTRATE FOR BIOCHIP AND BIOCHIP

TECHNICAL FIELD

The present invention relates to a biochip to which biologically relevant substances such as nucleic acids, peptides and saccharides are immobilized, and to a substrate therefor.

BACKGROUND ART

Biochips comprising a planar substrate and DNAs or proteins immobilized to the surface of the substrate include those prepared by the Affymettix method in which oligonucleotides are synthesized on the surface of the substrate using photolithography and those prepared by Stanford method in which probe DNAs or probe proteins are spotted to immobilize them to the surface of the substrate. It is well known that with both types of the biochips, fluorescence is detected after biochemical reactions with the target-analyte, and molecular recognition or diagnosis is carried out based on the pattern thereof. Among the above-described two methods, Affymetrix method has drawbacks in that stable immobilization and synthesis of long oligonucleotides are difficult because the oligonucleotides are synthesized on the surface of the substrate, and that the cost is also high. In the Stanford method, since small spots of probe DNAs, probe proteins or the like are placed on the surface of the substrate and the molecules to be recognized are immobilized by adsorption or covalent bonds, covalently bound amino groups, aldehyde groups or epoxy groups, or noncovalently bound poly-lysine is preliminarily provided on the surface of the substrates. However, in cases where the proposed substrate is made of an inorganic material such as glass, silicon, ceramics, glassy carbon or special carbon, the substrate has drawbacks in that it is cracked during manufacturing because of the high brittleness, and that long time and high costs are needed for the shaping. In cases where the substrate is made of an organic polymer resin, although the manufacturing is easy, the substrate has drawbacks in that focusing is difficult in detection because the planarity is poor and warping is large, and that S/N ratio is decreased by self-fluorescence. Further, there is also a drawback in that its planarity is changed during storage.
Patent Literature 1: JP 2001-128683 A
Patent Literature 2: Japanese Translated PCT Patent Application Laid-open No. 2005-510440

DISCLOSURE OF THE INVENTION

Problems to be Solved by the Invention

An object of the present invention is to overcome the above-described drawbacks in spotting the probe DNAs, probe proteins, probe saccharide chains or the like on the surface of the substrate in Stanford method, or in immobilization of microbeads or the like, and to provide a substrate for biochips with which the immobilization is easy, which is free from self-fluorescence, and which has a good flatness and surface precision.

Means for Solving the Problems

The present inventors intensively studied to discover that a substrate for biochips, to which biologically relevant substances can be easily immobilized, which is free from self-fluorescence, which is easy to manufacture and which has a good flatness and surface precision, can be obtained by using a substrate as a substrate for biochips, which substrate comprises a substrate body made of a metal and a carbon layer having functional groups, formed on the substrate body, thereby completing the present invention.

That is, the present invention provides a substrate for biochips, which substrate comprising a substrate body made of a metal, and a carbon layer having functional groups, which carbon layer is laminated on the substrate. The present invention also provides a biochip comprising the substrate for biochips according to the present invention to which a biologically relevant substance(s) is (are) immobilized. The present invention further provides a process for producing biochips, the process comprising the steps of providing the substrate for biochips, according to the present invention; and immobilizing a biologically relevant substance(s) on the substrate. The present invention still further provides a use of the above-described substrate according to the present invention for the production of biochips.

Effect of the Invention

By the present invention, a substrate for biochips, to which biologically relevant substances can be easily immobilized, which is free from self-fluorescence, which is easy to manufacture and which has a good flatness and surface precision, was first provided. Since the substrate body of the substrate for biochips, according to the present invention, is made of a metal, the substrate is not only easy to manufacture, but also free from cracking and chipping, so that it is easy to handle, and higher flatness and surface precision can be attained. Therefore, the problem that the optical system is hard to focus when detecting fluorescence does not occur. Moreover, since the substrate body is made of a metal, it does not emit fluorescence by itself. In addition, since the carbon layer has functional groups such as amino groups, biologically relevant substances can be easily immobilized.

BRIEF DESCRIPTION OF THE DRAWINGS

FIG. 1 shows the relationship between the amount of calmodulin and measured fluorescence intensity, which was resulted when calmodulin in a test sample was measured using a biochip prepared in an example of the present invention.

BEST MODE FOR CARRYING OUT THE INVENTION

As described above, the substrate body of the substrate for biochips, according to the present invention, is made of a metal. As the metal, metals selected from the group consisting of aluminum, titanium, stainless steel and alloys containing at least one of these metals, are preferred because they are easy to manufacture, excel in flatness because of high rigidity, and excel in smoothness after polishing because the surface is highly hard.

The substrate body is preferably flat and its surface is preferably smooth because if the substrate body is warped or if the surface thereof is irregular, diffuse reflection is large or the focusing is difficult in detection, so that the S/N ratio is decreased in detection. Therefore, it is preferred to anneal the substrate body under pressure to eliminate the strain and to promote the flatness after sizing such as punching, and, after grinding the surface to make it smooth, to increase the surface precision by further polishing the surface. These workings for attaining flatness and smoothness can be carried out by conventional metal working methods. In cases where the metal is aluminum or an aluminum alloy, since it is difficult to secure surface precision because the metal is soft, it is preferred to perform a hardening treatment such as electroless NiP plating or anodic oxidation. The surface roughness Ra of the substrate body is preferably less than 1 nm. Although the lower limit of Ra is not restricted, about 0.2 nm is usually close to the limit of working precision. The surface flatness of the substrate body is preferably less than 5 μm. The thickness of the substrate body is not restricted, and is usually about 0.5 mm to 2 mm. In cases where the substrate body is made of aluminum or an aluminum alloy, and a plated layer of NiP or the like is formed on the substrate body, or an oxide layer is formed on the substrate body by anodic oxidation of the surface, the thickness of the plated layer or the oxide layer is not restricted and is usually about 5 μm to 30 μm On the surface of the substrate body, a carbon layer having functional groups is laminated. In cases where the plated layer or oxide layer is formed, the carbon layer is formed thereon. That is, the carbon layer is formed on the surface of the substrate body indirectly through another layer. The carbon layer is a layer made of carbon, such as graphite, diamond, diamond-like carbon or amorphous carbon, and can be formed by sputtering method, vapor deposition method, CVD (chemical vapor deposition method) or the like. That is, the graphite layer can be formed by, for example, vacuum vapor deposition method using graphite particles as a vapor deposition source. The diamond layer can be formed by, for example, low pressure gas-phase synthesis method using a CVD apparatus having a heat filament. The diamond-like carbon can be formed by, for example, ion-sputtering method or high frequency plasma CVD method. Amorphous carbon can be formed by, for example, high frequency sputtering method. These methods can easily be carried out using commercially available apparatuses.

The carbon layer has functional groups for immobilizing a biologically relevant substance(s). The functional groups may be provided by binding the functional groups to the carbon layer after forming the carbon layer as described above. Examples of the functional groups include, but not limited to, amino group, aldehyde group, carboxyl group, sulfhydryl group and epoxy group. Among these groups, amino group is especially preferred because it is versatile and binding with biologically relevant substances is easy. These functional groups to be covalently bound to the carbon can be covalently bound to the carbon by cleaving C—C bond, C=C bond and/or C—O bond of the carbon by irradiation with plasma or ultraviolet light, and binding the resulting carbon radical with the functional groups or a compound(s) having the functional groups. For example, amino groups can be, as will be described in detail later in the Examples below, covalently bound to carbon by converting the oxygen in the air to ozone and reacting the resulting ozone with the carbon by irradiating the carbon layer with ultraviolet light in the air, then after evacuation, reacting chlorine gas with the resultant to chlorinate the carbon, and, after evacuation, reacting ammonia gas with the resultant to aminate the carbon. Alternatively, amino groups can also be directly introduced by irradiation with ammonia plasma. Still alternatively, amino groups can be generated on the surface by generating radicals by irradiating the substrate surface with argon plasma, converting the radicals to peroxide by air oxidation, and by reacting the resulting peroxide with allylamine or the like. Aldehyde groups can be obtained by, for example, converting the surface of the carbon to an acid chloride, and reducing the resulting acid chloride. Carboxyl groups may be obtained by, for example, converting amino groups to diazonium ions, converting the resulting diazonium ions to nitrile, and hydrolyzing the resulting nitrite. Carboxyl groups can also be obtained by oxidizing alkyl groups with potassium permanganate or the like. Sulfhydryl groups can be obtained by, for example, halogenating the surface of the carbon with light or the like, and reacting the generated halogenated alkyl with a thiol. Epoxy groups may be generated by treating the carbon-carbon double bonds with a peracid. Any of these reactions may be carried out based on the reactions in the field of organic synthetic chemistry, which are well-known by those skilled in the art. The functional groups are not necessarily bound to carbon by covalent bonds, but a compound(s) having the functional group(s) can be noncovalently attached by physical adsorption. For example, amino groups may be given to the carbon layer by physically adsorbing poly-lysine to the carbon layer, which poly-lysine is obtained by poly-condensation of lysine which is an amino acid having an amino group in its side chain. The density of the functional groups given to the carbon layer is not restricted, and usually about 50 pmol to 200 pmol, preferably about 100 pmol to 200 pmol per 1 $cm^2$ of the carbon layer.

By immobilization of a biologically relevant substance(s) to the above-described substrate for biochips, according to the present invention, a biochip can be obtained. Examples of the biologically relevant substances include nucleic acids such as DNAs and RNAs; various proteins, antibodies, enzymes and synthetic and natural peptides; saccharides such as polysaccharides and oligosaccharides; various lipids; and complexes thereof (glycoproteins, glycolipids, lipoproteins and the like). Further, cells can also be immobilized, so that the cell is also included within the scope of the term "biologically relevant substance". Still further, low molecular compounds such as coenzymes, antigen epitopes and haptens are also included within the scope of the term "biologically relevant substance" because they specifically interact with biopolymers such as enzymes and antibodies. These biologically relevant substances may be bound to the above-described carbon layer as they are, or they may be bound to the above-described carbon layer in the state of being immobilized to other carriers such as plastic beads.

Immobilization of the biologically relevant substance(s) to the carbon layer may be carried out by well-known methods through the above-described functional groups. For example, in cases where the functional groups are amino groups, as will be described in detail in the Examples below, biologically relevant substances may be immobilized to the substrate by converting the amino groups to the corresponding anhydride with bromoacetic acid and carbodiimide; reacting the resultant with amino groups to bromoacetylate the surface; and reacting the resultant with sulfhydryl groups in the biologically relevant substances such as peptides. Alternatively, the biologically relevant substances can be immobilized through glutaraldehyde by reacting the amino groups with the amino groups in the biologically relevant molecules. In cases where the functional groups are aldehyde groups, immobilization of the biomolecules desired to be immobilized can be attained by the reaction with the amino groups in the biomolecules. In cases where the functional groups are carboxyl groups, an ester is formed with N-hydroxysuccinimide, and the resulting ester can be bound with the amino groups in the biologically relevant substances. In cases where the functional groups are sulfhydryl groups, immobilization may be attained by selectively bromoacetylating the amino groups in the biologically relevant molecules. Alternatively, immobilization may be attained by binding the sulfhydryl groups with other sulfhydryl groups through disulfides. Further, sulfhydryl groups can be bound by selectively converting the amino groups at the site to be subjected to the immobilization, and binding the resultant with the sulfhydryl groups (for example, N-6 maleimide caproic acid is condensed with the amino groups). In cases where the functional groups are epoxy groups, the biologically relevant substances may be immobilized, similarly, by reaction of the epoxy groups with biologically relevant substance having maleimides.

The present invention will now be described more concretely by way of examples. However, the present invention is not restricted to the Examples.

EXAMPLE 1

Production of Substrate for Biochips

A high purity Al—Mg alloy plate (Mg content: 4% by weight) with a thickness of 1.2 mm was sized to 26 mm×76 mm by punching with a press. A plurality of the plates were stacked and annealed under pressure under an atmosphere at 340° C., thereby removing strain and attaining a flatness of not more than 5 μm. Thereafter, working of the end faces and chainfer (specifically, angle 45°, a length: 0.2 mm) was performed to prepare plates with a size of 25 mm×75 mm. Then each plate was ground with a double side grinding machine 16B produced by Speedfam, in which a sponge grindstone was mounted, to attain a thickness of 0.98 mm and a degree of parallelization of not more than 1 μm. The resulting plate was then subjected to, in the order mentioned, defatting, etching, acid activation, and zincate treatments.

More particularly, the plate was sequentially immersed in alkaline degreasing liquid AD-68F (50° C.) produced by Uyemura for 5 minutes, in sulfuric acid-phosphoric acid etching liquid AD-1101 F (80° C.) for 2 minutes, in nitic acid activating liquid (20° C.) for 1 minute, and in zincate liquid AD-301F3X (20° C.) for 30 seconds, thereby carrying out pretreatments. Thereafter, the plate was immersed in electroless NiP liquid NI-422 (90° C.) produced by Meltec Corporation for 2 hours to form a plated layer on both sides of the plate, each of which had a thickness of 12 μm. Each of the plated layers was polished by 2 μm with a double side grinding machine 16B produced by Speedfam using colloidal silica abrasive to obtain a plate having ultrasmooth surfaces. The plate had a thickness of 1.00 mm and a surface roughness Ra of 0.35 nm. The flatness, degree of parallelization and Ra were measured using a flat meter FT-50LD produced by Mizojiri, roundness measuring machine Talyrond produced by Rank Taylor Hobson and stylus-type surface roughness meter Talystep produced by Rank Taylor Hobson, respectively.

An amorphous layer was then formed on one surface of the plate using high frequency sputtering apparatus CFS-8EP produced by Toluda Seisakusho. Particularly, sputtering was carried out for 5 minutes under Ar atmosphere at 1.0 Pa, with a feed traveling wave power (Pf) of 1 kW, and with a reflected wave power (Pr) of 20 W. Then functional groups were given to the thus formed amorphous carbon layer. The functional groups were given by the following method: First, the substrate was set in a stainless steel vessel having a window made of a synthetic quartz, and irradiated with an ultraviolet lamp (lamp output power: 110 W) from a distance of 3 cm, which lamp emits an ultraviolet light having a component with a wavelength of 185 mm at 30% intensity and a component with a wavelength of 254 nm at 100% intensity, thereby subjecting the surface of the substrate to an ozone treatment. After evacuation, chlorine was then introduced to perform chlorine treatment (25° C., 5 minutes) under chlorine atmosphere at 13 Pa. Further, after evacuation, ammonia was introduced and amination treatment (25° C., 5 minutes) was carried out under ammonia atmosphere at 13 Pa. The amount of the amino groups on the substrate was 4.1 nmol/both surfaces. The amount of the amino groups was measured by a method in which the surfaces of the substrate were treated with hydrochloric acid and then the remaining hydrochloric acid was back titrated with aqueous sodium hydroxide solution (Japanese Patent Application No. 2005-069554).

EXAMPLE 2

Production of Biochip and Measurement of Using the Same

As the peptide to be immobilized to the biochip, a fluorescently labeled peptide having the following sequence (SEQ ID NO:1) was chemically synthesized: Ac-Cys-Gly-Lys(FAM)-Gly-Leu-Lys-Lys-Leu-Leu-Lys-Leu-Leu-Lys-Lys-Leu-Leu-Lys-Leu-Lys(TAMRA)-Gly-NH$_2$. Here, both "FAM" and "TAMRA" are fluorescent dyes. When FAM is excited with light, the excitation energy of FAM is transferred to TAMRA depending on the distance between FAM and TAMRA, and TAMRA emits fluorescence (called fluorescence resonance energy transfer, FRET-fluorescence). When a protein binds to the peptide, the helix structure of the peptide is immobilized, so that FRET florescence is increased. FRET is a phenomenon that energy is transferred from a donor molecule (FAM in this case) in the excited state to an acceptor molecule (TAMRA in this case) in the ground state, and fluorescence from the acceptor is observed. The peptide is known to specifically bind to calmodulin (CaM). Upon binding to CaM, the distance between FAM and TAMRA is decreased. The larger the amount of CaM, the higher the measured fluorescence intensity from TAMRA, so that the binding can be quantified.

The above-described labeled peptide was dissolved in 60% dimethylformamide (DMF) to a concentration of 2 μM. On the other hand, the amino groups on the substrate prepared in Example 1 were bromoacetylated. Specifically, this was carried out as follows: Bromoacetic acid (BrAcOH, Tokyo Chemical Industry, Mw=138.95, 2.00 mmol, 278 mg) and diisopropylcarbodiimide (DIC) (Aldrich Mw=126.20, 1.00 mmol, 126 mg) were dissolved in N-methylpyrrolidone (NMP) (3.33 ml), and the resulting solution was gently shaken at room temperature for 60 minutes to form bromoacetic anhydride. The thus obtained mixture was diluted with ultrapure water (Milli-Q water (trademark)) to a concentration of about 10 mM, thereby preparing a solution with a volume of about 100 ml. The solution was then added to the aminated substrate and the substrate was immersed in the solution at room temperature for 2 hours while occasionally light shaking the solution, thereby attaining bromination. The resulted substrate was washed with ultrapure water (Milli-Q water (trademark)), and dried under nitrogen. The above-described labeled peptide solution was spotted on the substrate to react the peptide with the above-described bromoacetylated amino groups, thereby to immobilize the peptide. The spotting was carried out using SpotBot apparatus produced by TeleChem International (California, U.S.) and using a microspotting pin also produced by TeleChem. International.

To the thus prepared labeled peptide-immobilized substrate, solutions containing different amounts of CaM (CaM was dissolved in 100 μM calcium chloride solution) were applied, and fluorescence was measured using a scanner (CR-BIO IIe produced by Hitachi Software Engineering).

The results are shown in FIG. 1. As shown in FIG. 1, the measured fluorescence intensity increased dependently on the amount of CaM. Thus, it was proved that a substance which specifically reacts with the biologically relevant substance immobilized on the chip can be quantified by the biochip according to the present invention.

The invention claimed is:

1. A substrate for biochips, said substrate comprising a substrate body comprising aluminum or an aluminum alloy; an NiP layer formed by electroless plating, said NiP layer being laminated on said substrate body and surface of said NiP layer being polished; and a carbon layer having functional groups, said carbon layer being laminated on said NiP plated layer to obtain a substrate body having a surface roughness (Ra) of less than 1 nm to which functional groups are added, wherein said functional groups are amino groups, aldehyde groups, carboxyl groups, sulfhydryl groups or epoxy groups, said groups being covalently bound to said carbon, or poly-lysine noncovalently bound to said carbon layer.

2. The substrate according to claim 1, wherein said carbon layer comprises at least one member selected from the group consisting of graphite, diamond, diamond-like carbon and amorphous carbon.

3. A biochip comprising a substrate according to claim 2, and a biologically relevant substance immobilized thereto.

4. A process for producing a biochip, said process comprising the steps of providing the substrate for biochips, according to claim 1; and immobilizing a biologically relevant substance(s) on said substrate.

5. A method of producing a substrate for biochips comprising
 (a) generating a substrate body made of aluminum or an aluminum alloy;
 (b) forming a NiP layer by electroless plating, said NiP layer being laminated on said substrate body;
 (c) polishing said NiP layer; and
 (d) laminating onto said NiP layer a carbon layer having functional groups, wherein said functional groups are amino groups, aldehyde groups, carboxyl groups, sulfhydryl groups or epoxy groups, said groups being covalently bound to said carbon, or poly-lysine noncovalently bound to said carbon layer, to produce a substrate for biochips having a substrate body with a surface roughness (Ra) of less than 1 nm.

* * * * *

SEQUENCE LISTING

<160> NUMBER OF SEQ ID NOS: 1

<210> SEQ ID NO 1
<211> LENGTH: 20
<212> TYPE: PRT
<213> ORGANISM: Artificial Sequence
<220> FEATURE:
<223> OTHER INFORMATION: Synthetic peptide immobilized on a biochip

<400> SEQUENCE: 1

Cys Gly Lys Gly Leu Lys Lys Leu Leu Lys Leu Leu Lys Lys Leu Leu
1               5                   10                  15

Lys Leu Lys Gly
            20